United States Patent [19]

Schneider et al.

[11] 4,399,221

[45] Aug. 16, 1983

[54] ENZYME PRODUCTION AND PURIFICATION

[75] Inventors: Michel Schneider, Troinex; Christian Guillot, Carouge, both of Switzerland; Andre Ayerbe, Roche-sur-Foron, France

[73] Assignee: Fisons Limited, London, England

[21] Appl. No.: 277,706

[22] Filed: Jun. 26, 1981

[30] Foreign Application Priority Data

Jul. 5, 1980 [GB] United Kingdom ............... 8022105

[51] Int. Cl.³ .................. C12N 9/10; C12P 19/04; C12P 19/08
[52] U.S. Cl. .................. 435/193; 435/813; 435/818; 435/101; 435/103
[58] Field of Search .................. 435/101, 103, 193

[56] References Cited

U.S. PATENT DOCUMENTS 2,673,828 3/1954 Koepsell et al. ................... 435/193
2,686,147 8/1954 Tsuchiya et al. ................... 435/193
3,060,103 10/1962 Kaufmann et al. ................. 435/193
4,309,505 1/1982 Smith et al. ....................... 435/193

*Primary Examiner*—Lionel M. Shapiro
*Attorney, Agent, or Firm*—Merriam, Marshall & Bicknell

[57] ABSTRACT

There is described a process for the production of a polysaccharide-producing enzyme, which comprises fermenting an appropriate enzyme producing organism in aqueous sucrose, characterized in that the sucrose concentration is maintained at between 1 and 10 g/l throughout all but the last part of the fermentation and that the dissolved oxygen content of the fermentation is controlled.

There is also described a method for the purification of a polysaccharide producing enzyme, which comprises absorbing a mixture containing the enzyme on an anionic resin and removing the enzyme from the resin with a sugar containing eluant, and a novel highly purified form of polysaccharide producing enzyme.

3 Claims, No Drawings

ENZYME PRODUCTION AND PURIFICATION

This invention relates to the preparation and purification of a polysaccharide-producing enzyme and to materials containing high concentrations of enzyme.

It is known that certain microorganisms can be cultivated in such a way that culture liquors are obtained rich in polysaccharide-producing enzymes. Certain enzymes, either in situ in the fermentation liquors, or isolated as such, are capable of converting sucrose into dextran. In this known process, e.g. as described in U.S. Pat. No. 2,686,147 the enzyme-producing organisms are cultured in a sugar medium where the production of the dextran itself is minimised, and maximum production of the enzyme, e.g. dextransucrase, is realised.

We have discovered that the yields of the enzyme may be considerably increased by proper control of culture conditions, particularly the pH, the sucrose concentration (much lower than previously) and the degree of aeration (much higher than previously). We have moreover, discovered that enzyme of considerably increased purity may be produced, that the enzyme can, under certain circumstances, be produced in the substantial absence of dextran, that sucrose limited growth in the production broth is, contrary to the teaching of the art, advantageous, and that enzymes may be produced which have no or minimal invertase activity and produce dextrans of the same physical properties as dextrans produced by normal bacterial fermentations.

According to the invention we provide a process for the production of a polysaccharide-producing enzyme, e.g. dextransucrase, which comprises fermenting an appropriate enzyme producing organism in aqueous sucrose, characterised in that the sucrose concentration is maintained at between 1 and 10 g/l throughout all but the last part of the fermentation and that the dissolved oxygen content of the fermentation is controlled. We prefer the sucrose concentration to be between 5 to 10 g/l.

By the term 'the last part of the fermentation' we mean when there is no more growth and no more significant enzyme synthesis.

During the last part of the fermentation, substantially all the sucrose, e.g. to a level of less than 5 g/l and preferably less than 1 g/l, should be used up by metabolism to prevent the formation of excess dextran in situ. The presence of a small amount of dextran, e.g. from 0.1 to 3.0% w/w in the fermentation product can however be advantageous, e.g. in the subsequent isolation of the enzyme. However the more dextran there is present the more viscous is the medium and the more difficult the separation of the cells from the medium tends to be.

If the sucrose concentration is allowed to fall to too low a value during the fermentation we have found that, even if the level is subsequently increased to within the desired range, a considerable decrease in the overall yield of enzyme occurs. We therefore prefer the increase in enzyme activity to substantially parallel growth of the biomass.

We prefer the dissolved oxygen level to be maintained at a high level, e.g. between 100 and 40%, and preferably between 80 and 40% throughout the fermentation. In particular we prefer the dissolved oxygen to be high at the beginning of the fermentation and to be permitted to fall as the fermentation progresses. The dissolved oxygen level can be controlled by the rate at which the fermentation is agitated, e.g. stirred, and/or by the rate of addition of air or oxygen.

The amount of sucrose in the fermentation mixture may be measured by a variety of methods, e.g. high pressure liquid chromatographic analysis, or by relating the consumption of sucrose to the amount of alkali needed to maintain a constant pH, and the result may be used to determine the desired rate of addition of further sucrose. One or more sucrose measurements may be necessary during each fermentation.

The continuous or batch addition of sucrose to the fermentation medium to maintain the concentration of the sucrose in that medium, i.e. a 'fed-batch' process, forms a specific feature of this invention. This process is advantageous as compared to a continuous process in that the risk of mutation of the bacterial strain is minimised.

We prefer the fermentation to be carried out for a period of from about 5 to 15 hours.

We prefer the pH throughout substantially all of the fermentation to be from about 6.0 to 7.0 and preferably to be about 6.7.

The pH may be controlled within the limits of 6.0 to 7.0 by, for example, buffers, such as the well-known phosphate type of buffer, or by addition of sufficient amounts of water soluble alkali, e.g. sodium or potassium hydroxide, to maintain the desired pH. The latter method may be accomplished by the use of automatic pH controlling devices, and is preferred. If desired the sucrose and alkali may be mixed in appropriate proportions immediately before addition to the fermentation and the mixture may be added when the pH of the fermentation reaches a pre-set level. Alternatively the alkali and the sucrose may be added separately, but simultaneously.

Buffers which may be used to maintain the pH within the range of 6 to 7 are, for example, phosphate buffers, citrate buffers, bicarbonate buffers, and the like.

The mineral and assimilable nitrogen requirements for the fermentation are essentially those familiarly encountered in the art for the production of dextran. For example, there may be used protein or proteinaceous materials, such as yeast extract, corn steeping liquor, distillers' solubles, soy meal products, and the like. However we prefer to use a high concentration, e.g. greater than 15 g/l, of potassium phosphate.

Cell separation at the end of the fermentation may be accomplished by a variety of methods, e.g. the cells may be filtered or centrifuged from the medium.

We prefer to carry out the fermentation at a temperature of 20°–35° C., and more preferably 20° to 30° C. and desirably at 23°–25° C.

The above procedures can, under certain circumstances, produce aqueous fermentation broths containing enzyme concentrations of more than 150, preferably more than 200, and more preferably more than 250 DSU/ml enzyme. Enzyme concentrations of up to 400 DSU/ml and higher may be obtained under appropriate conditions.

Any organism of the genera Leuconostoc, Aerobacter, Streptobacterium, Betabacterium, Bacillus, Lactobacillus, Streptococcus and the like, known to produce the polysaccharides, dextran, levan, or mixtures thereof in aqueous culture media may be used. We particularly prefer to use Leuconostoc mesenteroides.

According to a further feature of the invention we provide a method for the purification of a polysaccharide producing enzyme, which comprises absorbing a mixture containing the enzyme on an anionic resin and removing the enzyme from the resin with a sugar containing eluant.

The anionic resin is preferably a diethylaminoethyl (DEAE)-cellulose resin, though other anionic resins may also be used (e.g. DEAE-Sephadex and DEAE-Sepharose), and the sugar used in the eluant may be sucrose or another sugar. We prefer to use a sugar other than sucrose, e.g. fructose, maltose or α-methylglucoside, in the eluant as the production of dextran on the resin is thereby minimised. The concentration of the sugar in the eluant is preferably between 0.1 and 8%, e.g. 1 to 5%. Specifically we prefer a mixture of 0.1 to 1% of sucrose together with 1 to 5% of alpha methylglucoside.

We prefer to carry out the purification at a temperature of below about 10° C., more preferably below 8° C., e.g. at 4° C. The purification should of course be carried out at a temperature at which the medium is liquid.

The mixture containing the enzyme and dextran is preferably obtained by solvent, e.g. ethanol, precipitation of the fermentation broth in which the enzyme (and some dextran) has been produced.

In the precipitation of the enzyme with ethanol, the salt content of the medium is of significance, the higher the salt content the more ethanol is required to precipitate the enzyme. In the procedure used for optimal enzyme production a large amount of alkali, e.g. sodium hydroxide, is added and therefore the salt content at the end of fermentation is high. 30% (v/v) Aqueous ethanol was found to be suitable to precipitate the enzyme from such a fermentation media. Higher ethanol concentrations (40% v/v) had a detrimental effect on the enzyme activity. If the broth was dialysed to remove salts the enzyme could be precipitated to give a yield of 90% with 25% ethanol.

Another factor of importance in the isolation of the enzyme is the dextran content of the fermentation broth.

If pH is regulated at 6.7 during fermentation, the dextran content of the broth is nearly zero. Under these conditions the enzyme could not be precipitated efficiently with ethanol. Yields of 10-15% were obtained using 35% v/v ethanol. However, if some sucrose was added to the broth before precipitation, dextran was formed in situ and the enzyme could be precipitated efficiently. We prefer the dextran content to be up to that produced from 1 g of sucrose per $1-1.5\times10^5$ DSU of enzyme.

Fermentation broths containing high enzyme concentrations yielded a much purer enzyme after ethanol precipitation than has been previously observed. With the improved procedures of the present invention, crude enzyme containing more than 100, and up to 300 or more, DSU/mg dry weight can be obtained.

According to the invention we also provide a purified polysaccharide producing enzyme containing more than 800 and preferably more than 3,000 DSU/mg protein.

The invention is illustrated, but in no way limited by the following Examples.

EXAMPLE 1

A three step procedure was used to prepare the inoculum. The composition of the medium used for the inoculum was as follows:

| | | |
|---|---|---|
| Sucrose: | 40g | |
| Molasses: | 20g | |
| Na$_2$HPO$_4$: | 0.4g | Medium A |
| Yeast extract (Difco): | 5g | |
| Water: | 1 liter | |

The pH was adjusted to 7.5 with 0.1 g NaOH. This medium was sterilised for 20 minutes at 115° C.

Step 1

100 ml of sterile medium A were introduced into a culture flask and inoculated with one ampoule of freeze-dried *leuconostoc mesenteroides* (ref. Fisons C31 NCIB 8710). This culture flask was kept at 27° C. for 14 hours on a shaker.

Step 2

10 ml aliquots of the primary culture were transferred to 6 Erlenmeyer flasks, each containing 100 ml of sterile medium A. These flasks were incubated at 27° C. for 10 hours on a shaker.

Step 3

The fermenter was filled with 10 liters of the following medium:

| | | |
|---|---|---|
| Sucrose: | 40g/liter | |
| Yeast extract (containing 10% nitrogen, 50% of the nitrogen being available as alpha amino nitrogen): | 40g/liter | |
| K$_2$HPO$_4$: | 20g/liter | Medium B |
| R salts: | 0.5% (by volume) | |
| Antifoaming additive (silicone SAG 120): | 1 ml | |
| R salts are: | | |
| MgSO$_4$.7H$_2$O | 4.0g | |
| NaCl | 0.2g | |
| FeSO$_4$.7H$_2$O | 0.2g | |
| MnSO$_4$.H$_2$O | 0.2g | |
| H$_2$O | 100 ml | |

This medium was sterilised (20 min, 115° C.), cooled to 23° C. and the pH adjusted to 7.2. Air was introduced at the rate of 2 vvm and agitation was started.

600 ml of the secondary culture were introduced into the fermenter and left for 13 hours at 23° C. The pH was not regulated.

Under these conditions, the biomass concentration obtained in the final inoculum was 3 g/liter in an experiment P$_2$ and 4 g/liter in an experiment P$_3$. Six liters of inoculum in experiment P$_2$ and 4.5 liters in an experiment P$_3$ were transferred to the main fermenter (300 liters), thereby obtaining an initial biomass concentration of 0.06 g/liter.

Fermentation Medium

In the two experiments the following initial medium was used

| | | |
|---|---|---|
| Sucrose: | 10g/liter | |
| Yeast extract: | 40g/liter | |
| K$_2$HPO$_4$: | 20g/liter | Medium C |
| R salts: | 0.5% (by volume) | |
| Antifoaming additive (Silicone SAG 120): | 0.1% (by volume) | |

All the constituents were dissolved in a small amount of tap water and then transferred to the fermenter. Tap water was then added up to a final volume of 300 liters and the pH was adjusted to 7.1–7.2.

The medium was sterilised at 115°–118° C. for 30 minutes and then cooled. During cooling, sterile air was introduced in order to maintain a slight over pressure (0.2 atm) in the fermenter. The temperature in the fermenter was then regulated at 23° C. and sterile air introduced at a rate of 1 vvm. Agitation was maintained. Industrial grade sodium hydroxide solution (32%) was used for pH regulation. Additional sucrose was made up as a 60% solution in tap water and sterilised.

The pH, dissolved oxygen concentration and temperature were continuously recorded. In addition, once an hour samples were withdrawn and the growth level (as measured by optical density at 590 nm), the sugar level (sucrose and fructose) and the enzyme activity were determined. The hourly composition of sucrose and NaOH was recorded.

Conduct of the Fermentation

100 Liters of a sucrose solution (600 g/liter) were prepared and sterilised (115° C., 20 minutes) in an autoclave.

The inoculum was added. Soon after inoculation the pH started to decrease; when it reached 6.7 it was automatically regulated at this value by the addition of a 32% solution of sodium hydroxide. After 3.5 hours in $P_2$ (4 hours in $P_3$), the Optical Density$_{590}$ ($OD_{590}$) reached 0.1, and the sucrose level in the fermenter was 6.5 g/liter in $P_2$ and 6.3 g/liter in $P_3$. Sucrose was then added at the rate of 800 g sucrose per hour. One hour later, the rate of sucrose addition was increased in 1400 g/hr. The rate of sucrose addition was then modified every hour during the entire fermentation. Knowing the hourly sucrose level in the fermenter (by High Pressure Liquid Chromatography) and knowing the amount of sucrose added, the amount of sucrose consumed during the elapsed hour was determined. From this value the consumption during the next hour was predicted and the rate of sucrose addition adjusted accordingly.

During fermentation, the level of oxygen in the fermenter was adjusted by varying the speed of agitation in order to obtain an oxygen level decreasing regularly from an initial 100% to about 40–70% at the end of the fermentation.

A slight over-pressure was maintained in the fermenter during the entire fermentation.

After 14 hours of fermentation, when the $OD_{590}$ levelled off at 0.91 in $P_2$, 1.19 in $P_3$, the addition of sucrose was stopped, but the pH regulation was maintained for a further hour. During this period the sucrose remaining in the fermenter was used up. After 15 hours, the pH regulation was stopped. The fermenter was then cooled to 8° C. and left overnight. Aeration was maintained at one vvm with agitation.

The next day the pH in the fermenter was between 5.4 and 5.8, and the biomass concentration was 7.2 g/liter in $P_2$ and 9.6 g/liter in $P_3$.

Results

The results obtained in experiments $P_2$ and $P_3$ are reported in Table I.

TABLE I

|  | $P_2$ | $P_3$ |
|---|---|---|
| Initial conditions | Sucrose: | 3 kg |
|  | Yeast extract: | 12 kg |
|  | $K_2HPO_4$: | 6 kg |
|  | R salts: | 1.5 l |
|  | Antifoaming additive: | 30 ml |
|  | Town water: | to 300 l |
| Additions during fermentation |  |  |
| Sucrose | 31.8 kg | 20.7 kg |
|  | (= 63.6 kg (53 l) of a 60% w/v aqueous sucrose solution) | (= 41.4 kg (34.5 l) of a 60% W/V aqueous sucrose solution) |
| 32% w/v aqueous NaOH solution | 18.8 kg | 17.2 kg |
|  | (= 13.9 l, = 150.2 moles NaOH) | (= 12.7 l, = 137.5 moles NaOH) |
| Final conditions |  |  |
| Enzyme activity | 290 DSU/ml | 260 DSU/ml |
| Biomass concentration | $OD_{590} = 0.95$ (7.2g/l) | $OD_{590} = 1.20$ (9.6g/l) |
| Final volume (assumed) | 366.9 l | 347.2 l |

In both experiments the sucrose level in the fermenter was regulated within reasonable limits (between 6 and 9 g/liter in $P_2$ and between 2 and 7 g/liter in $P_3$).

The oxygen level in the fermenter was maintained above 40% in $P_2$ by gradually increasing the speed of agitation.

In both cases, at the end of the exponential growth phase, a secondary growth phase starting 10 hours after the beginning of fermentation and lasting about two hours was observed.

EXAMPLE 2

800 Ml of a sucrose solution (600 g/l) were prepared and sterilised (115° C., 20 minutes).

The fermentation medium was prepared as described in Example 1 using 10 g/l sucrose. After sterilisation, cooling and regulation at 23° C. the pH was set at 7.1 and the aeration at 4 vvm with agitation. The medium was inoculated with 3 Erlenmeyer flasks (300 ml for 5 liters) of inoculum prepared as in Example 1.

Soon after inoculation the pH started to decrease; when it reaches 6.7 it was regulated at this value by the addition of 5 N NaOH. After 5 hours, the $OD_{590}$ reached 0.1 and the remaining sucrose concentration in the fermenter was 5–6 g/l. Sucrose was then added using a peristaltic pump with variable flow rate. The initial rate of sucrose addition was 15 g/hr. After one hour this rate was increased to 30 g/hr. After 7 hours of fermentation the rate was increased to 50 g/hr, after 8 hours to 70 g/hr and after 9 hours to 90 g/hr. The rate of sucrose addition was then kept at this value until the optical density reached 1.1–1.2. At that time a reduction in the NaOH consumption was noted. The addition of sucrose was stopped but the pH regulation was maintained for 0.5–1 hr. During this period the sucrose remaining in the fermenter was used up. pH regulation was then stopped. The pH then decreased rapidly to 5.2–5.0 and the fermentation broth was processed for enzyme recovery.

The results are shown in the following Table II.

TABLE II

| Initial conditions | Sucrose: | 50g |
|---|---|---|
| | Yeast extract: | 100g |
| | $KH_2PO_4$: | 100g |
| | R* salts: | 25 ml |
| | Initial volume: | 5 liters |
| Additions during fermentation | Sucrose: | 480g (800 ml) |
| | NaOH 5N: | 450 ml |
| Final conditions | Enzyme activity: | 230 DSU/ml |
| | Final volume: | 6.25 liters |

EXAMPLE 3

(Isolation of Enzyme)

Ethanol at 0°–5° C. was added up to a final concentration of 25% to previously centrifuged fermentation broth. This treatment gives a significant reduction in the volume of materials to be handled and a high recovery of enzyme activity (about 85%).

Two batches of enzyme isolated in this way had the following characteristics:

| | Enzyme No 1 | Enzyme No 2 |
|---|---|---|
| Specific activity (DSU/mg protein) | 331 | 162 |
| Reducing sugars | 3.7% | 3.1% |
| Salt content (estimated) | 14.5% | 14.0% |
| Dextran content | 20.0% | 42.0% |

Both enzymes were produced under the same conditions.

EXAMPLE 4

(Variation of Dissolved $O_2$)

Five experiments were carried out in a laboratory fermenter using the same media as in Example 1. Temperature was 23° C., pH regulated at 6.7 and sucrose added continuously. In experiments A, B and C the dissolved $O_2$ dropped slowly from an initial 100% to about 40% at the end of the fermentation. In experiment D dissolved $O_2$ dropped to zero half way through the fermentation. In experiment E $O_2$ in excess of requirement, i.e. as close to 100% as possible, was maintained throughout the run and in F the fermentation was not aerated. The results are given below:

| Dissolved oxygen | | Max Enzyme Yield |
|---|---|---|
| 100%–40% | A | 280 DSU/ml |
| | B | 260 DSU/ml |
| | C | 400 DSU/ml |
| 100%–0% | D | 105 DSU/ml |
| 100% | E | 180 DSU/ml |
| No $O_2$ | F | 150 DSU/ml |

EXAMPLE 5

(Purification)

The crude enzyme (10000 DSU) was applied in 0.3 M acetate buffer pH 5.0 on top of a 45 ml column of the anionic resin DEAE A 25 (Pharmacia) and eluted with the same buffer. No enzyme activity was released. After 72 ml, the buffer was changed to 1 M NaCl, 0.3 M acetate buffer pH 5.0. Nearly all foreign material present in the crude enzyme preparation was then released. Finally the enzyme was eluted using the same buffer to which 1% sucrose and 1% maltose hydrate had been added.

The fractions having enzyme activity were pooled and then concentrated by ultrafiltration using an XM 50 membrane (Amicon) and freeze dried. The enzyme preparation obtained had a specific activity of 3250 DSU/mg protein which is significantly higher than all formerly described pure enzyme preparations. The recovery yield of the enzyme was 67%.

Elution of the purified enzyme can also be obtained by using 0.5% sucrose, or even less, together with 1–5% α-methyl-glucoside.

The following table shows the results obtained with an enzyme sample and various elution media. These assays were carried out on 2 ml columns.

TABLE

| Conditions: | Absorption of the crude enzyme (200 DSU) in 0.3M acetate buffer, pH 5.0, on a DEAE A 25 resin (2 ml) Washing of the column with 1M NaCl, 0.3M acetate buffer Elution with 1M NaCl, 0.3M acetate buffer containing various sugar concentrations (see below) | |
|---|---|---|
| Sugar concentrations in the elution medium | | Recovery of enzyme |
| 1% sucrose, | 5% α-methylglucoside | 69% |
| 1% sucrose, | 1% α-methylglucoside | 100% |
| 0.5% sucrose, | 5% α-methylglucoside | 100% |
| 0.5% sucrose, | 1% α-methylglucoside | 76% |
| 0.2% sucrose, | 5% α-methylglucoside | 81% |
| 0.1% sucrose, | 5% α-methylglucoside | 79% |
| — | 5% α-methylglucoside | 0% |

EXAMPLE 6

The procedure of Example 2 was adapted for continuous operation with satisfactory results.

In the above Examples the bacterial growth and enzyme activity are determined, and DSU are defined, as follows.

(a) Measurement of Bacterial Growth (biomass)

Growth is measured by determining the optical density (O.D.) at 590 nm of a sample diluted 25 times with saline (NaCl 0.9%). For O.D. values higher than 0.6 the samples are diluted 50 times and the O.D. measured is multiplied by two.

Optical density measurements provide rapid information on the growth of the bacteria. O.D. values are proportional to dry cell concentrations. Dry cell concentrations are determined by filtration of an aliquot on a pre-weighted Millipore filter (0.22μ) and weighing of the filter after drying (20 minutes, 60° C.).

(b) Determination of Enzyme Activity

Enzyme activity is determined by measuring the fructose released using Hostettler's method (Helv. Chim. Acta, 34, 2132, 1951).

(c) One DSU (dextransucrase unit) is the amount of enzyme which converts 1 mg sucrose to dextran in one hour (releasing 0.52 mg fructose) at 25° C. The assay is conducted on a 5% sucrose solution in 0.1 M acetate buffer at pH 5.2.

We claim:

1. A process for the production of a polysaccharide-producing enzyme comprising:

fermenting bacteria capable of producing dextran, levan or mixtures thereof in an aqueous sucrose solution at a temperature of 23°–25° C.;

maintaining the sucrose concentration in said solution between 1 and 10 g/l during the fermentation by addition of sucrose solution until fermentation is almost complete, then permitting the sucrose concentration to fall below 1 g/l, and controlling the dissolved oxygen content of the fermentation medium from an initial value of 80–100% of saturation to a final value of 40% of saturation.

2. A process according to claim 1, wherein the pH of the fermentation medium is controlled at from 6.0 to 7.0.

3. A process according to claim 2, wherein the pH is controlled by the addition of water soluble alkali.

* * * * *